United States Patent
Ohgushi

(12) 
(10) Patent No.: US 6,989,030 B1
(45) Date of Patent: Jan. 24, 2006

(54) TRANSPLANT MATERIAL AND METHOD FOR FABRICATING THE SAME

(75) Inventor: Hajime Ohgushi, Kashihara (JP)

(73) Assignee: Japan Tissue Engineering Co., Ltd., Aichi (JP)

( * ) Notice: Subject to any disclaimer, the term of this patent is extended or adjusted under 35 U.S.C. 154(b) by 363 days.

(21) Appl. No.: 10/129,916

(22) PCT Filed: Nov. 9, 2000

(86) PCT No.: PCT/JP00/07892

§ 371 (c)(1),
(2), (4) Date: May 10, 2002

(87) PCT Pub. No.: WO01/34218

PCT Pub. Date: May 12, 2001

(30) Foreign Application Priority Data

Nov. 11, 1999 (JP) ............................ 11/320509

(51) Int. Cl.
A61F 2/28 (2006.01)
C12N 5/00 (2006.01)

(52) U.S. Cl. .................. 623/16.11; 623/23.61; 424/423; 424/422; 435/395; 435/325

(58) Field of Classification Search ............. 424/423, 424/422; 623/23.6; 435/325, 395, 402
See application file for complete search history.

(56) References Cited

U.S. PATENT DOCUMENTS

| | | | | |
|---|---|---|---|---|
| 2,679,245 A | * | 5/1954 | Timmermans | 623/23.11 |
| 4,164,794 A | * | 8/1979 | Spector et al. | 623/23.6 |
| 4,878,914 A | * | 11/1989 | Miwa et al. | 623/23.56 |
| 5,306,305 A | * | 4/1994 | Lee | 435/325 |
| 5,643,789 A | * | 7/1997 | Ducheyne et al. | 435/402 |
| 6,541,024 B1 | * | 4/2003 | Kadiyala et al. | 424/426 |

FOREIGN PATENT DOCUMENTS

| | | |
|---|---|---|
| JP | 03-045267 | 2/1991 |
| JP | 07-116184 | 5/1995 |
| JP | 08-112341 | 5/1996 |
| WO | WO 93/25246 | 12/1993 |
| WO | WO 94/04657 | 3/1994 |
| WO | WO 97/05238 | 2/1997 |
| WO | WO 97/40137 | 10/1997 |

OTHER PUBLICATIONS

Nijweide et al., 1982. Bone formation and calcification by isolated osteoblastlike cells. J. Cell Biol. 93: 318-323.*
Pittenger et al., 1999. Multilineage potential of adult human mesenchymal stem cells. Science 284: 143-147.*
Mackie EJ. 2003. Osteoblasts: novel roles in orchestration of skeletal architecture. Int J Biochem Cell Bio 35: 1301-1305.*

* cited by examiner

*Primary Examiner*—Irene Marx
*Assistant Examiner*—Lora E Barnhart
(74) *Attorney, Agent, or Firm*—Fish & Richardson P.C.

(57) ABSTRACT

A transplant material which is capable of imparting desired mechanical properties, elevating bone tissue repair speed and improving biocompatibility. This transplant material comprises an artificial and biologically inactive material, which is to be implanted in vivo as a substitute for bone tissue, and at least one type of cells selected from among osteoblasts and precursory osteoblasts which are adhered to the surface of the artificial material so that the artificial material is coated with the bone matrix produced by the cells. The artificial material involves not only a biologically inactive material but also a biologically inactive material coated with a biologically active substrate. This transplant material is produced by culturing mesenchymal stem cells collected from a living body to differentiate into at least one type of cells selected from among osteoblasts and precursory osteoblasts and then culturing the cells together with the artificial material to thereby adhere the differentiated cells on the surface of the artificial material and coat the surface of the artificial material with the bone matrix produced by the differentiated cells.

9 Claims, 1 Drawing Sheet

TRANSPLANT MATERIAL AND METHOD FOR FABRICATING THE SAME

BACKGROUND OF THE INVENTION

The present invention relates to a bone tissue implant and a fabricating method of the implant. The implant of the present invention can be used as artificial joints, bones, or tooth roots, for surgical treatment of humans, pets, domestic animals, and the like. Specifically, it can be used as a replacement for bone tissues in a living body.

It is well known that an artificial joint is composed of a stem portion, a head portion, and an acetabular portion. The stem and head portions of the conventional artificial joint are composed of bioinert materials, e.g., titanium alloy, or alumina ceramics. These materials retain greater strength and resist corrosion. The acetabular portion of the conventional artificial joint is composed of high-density polyethylene, which offers adequate resiliency and biotolerance. When the above artificial joint is implanted as a replacement of a damaged hip joint, the stem portion is implanted in a hollow part perforated for the upper part of a femur through bone cement made of polymethyl methacrylate (PMMA), and the acetabular portion is implanted in a coxal bone located in the lower part of a pelvis through the bone cement. The implanted artificial joint sufficiently functions as a hip joint, retaining greater strength and avoiding corrosion.

However, it is well known that the PMMA bone cement generates very high heat of polymerization when methyl methacrylate monomer is polymerized to harden. Therefore, the problem exists that the heat of polymerization seriously damages bone tissues where the bone tissues and bone cement contact. To solve the above problems, a following therapy has been performed, which uses natural healing power of a patient. In the therapy, the operation in which the stem portion and the acetabular portion of the artificial joint were implanted was performed so that these portions directly contact the bone tissues without using bone cement. Subsequently, the patient was made to keep quiet in bed until the artificial joint was sufficiently fixed to the bone tissues.

When the above therapy was performed, the mesenchymal stem cells which exist in patient bone marrow migrate to the clearance between the artificial joint and the bone tissues and then are adhered. Subsequently, the adhered mesenchymal stem cells proliferate and differentiate to osteoblasts having high bone repair activity. Then, the osteoblasts produce bone matrix. The bone matrix covers the surfaces of the artificial joint and bone tissues to fill the clearance. As a result, the artificial joint is fixed.

Japanese Laid-Open Patent Publication No. 3-45267 discloses filling materials for a bone defective part and a bone vacant part. The filling materials are composed of body fluid containing osteoblasts and/or osteoprogenitor cells, which is obtained from an animal, and calcium phosphate compounds. The filling materials for the bone defective part and the bone vacant part are prepared by the steps of adsorbing the body fluid from the animal itself to be treated to porous or granular calcium phosphate compounds, and culturing artificially, if necessary. The bone defective part and the bone vacant part of the animal are filled with the resultant filling materials for the bone defective part and the bone vacant part. The filling materials have excellent biocompatibility, and do not cause xenobiotic reaction and inflammatory reaction. In addition, the leakage of the filling materials from a filling site is very little. Therefore, rapid formation of new bone may be expected.

On the other hand, the conventional artificial joint has possibility for damaging the living tissues, such as circumferential bone tissues, since PMMA bone cement for connecting the artificial joint to the bone tissues generates a heat during the polymerization, and also the residual monomer elutes out. Therefore, when the artificial joint is used under a mechanically (i.e., physically) severe condition, the boundary face between the stem or acetabular portion and bone tissues surrounding it is destroyed. In addition, there is remarkably high possibility that the artificial joint will become loose or disengaged.

Further, the above-mentioned conventional therapy using natural healing power requires a long period of time until the mesenchymal stem cells to the surfaces of the artificial joint and bone tissues, and then produce bone matrix. In particular, an aged living body requires a very long period of time for being completely recovered, since they have less mesenchymal stem cells in their body and bone tissue repair speed by osteoblasts and osteoprogenitor cells is remarkably slow.

In the conventional filling materials for the bone defective part and the bone vacant part, porous or granular calcium phosphate ceramics are used as a substrate. The ceramics composed of these substrates have low mechanical strength, and are typically brittle. Therefore, they could not be used for the site in which a large load is applied or elastic deformation is required.

BRIEF SUMMARY OF THE INVENTION

The objectives of the present invention are to solve the above problems of the prior art; to provide implant materials, which give desired mechanical properties as well as have improved bone tissue repair speed and biocompatibility; and to provide a method for fabricating such implant materials.

To achieve the above objectives, the first aspect of the present invention includes implant materials, which are obtained by the steps of adhering cells to a bioinert artificial material to be implanted in a living body as a replacement of bone tissue, wherein the cells are at least one kind of cells selected from osteoblasts and osteoprogenitor cells; and coating the artificial material with bone matrix that is produced by the adhered cells.

Another aspect of the present invention includes implant materials in which the artificial material is composed of at least one of materials selected from titanium, titanium alloy, stainless steel, cobalt-chromium alloy, cobalt-chromium-molybdenum alloy, alumina ceramics, carbon ceramics, zirconia ceramics, silicon carbide ceramics, silicon nitride ceramics, glass ceramics, polyethylene, polystyrene, polytetrafluoroethylene, polyurethane, polyvinyl alcohol, polypropylene, polycarbonate, polymethyl methacrylate, methacrylate polymer, silicone resin, and bioabsorbable polymer.

The further aspect of the present invention includes implant materials in which the surface of the artificial material is coated with bioactive substrate.

The further aspect of the present invention includes implant materials in which the bioactive substrate includes at least one of materials selected from hydroxyapatite, tricalcium phosphate, calcium-deficient apatite, amorphous calcium phosphate, tetracalcium phosphate, octacalcium phosphate, fluorapatite, carbonate-apatite, calcium pyrophosphate, brushite, monetite, calcium carbonate, glass ceramics containing apatite, glass ceramics containing calcium metaphosphate, and bioglass.

The artificial material may be composed of at least one of metallic materials selected from titanium, titanium alloy, stainless steel, cobalt-chromium alloy, and cobalt-chromium-molybdenum alloy.

The artificial material may be composed of at least one of ceramic materials selected from alumina ceramics, carbon ceramics, zirconia ceramics, silicon carbide ceramics, silicon nitride ceramics, and glass ceramics.

The artificial material may be composed of at least one of synthetic resin materials selected from polyethylene, polystyrene, polytetrafluoroethylene, polyurethane, polyvinyl alcohol, polypropylene, polycarbonate, polymethyl methacrylate, methacrylate polymer, silicone resin, and bioabsorbable polymer.

The bone matrix may include a growth factor secreted from at least one kind of cells selected from marrow cells, mesenchymal stem cells, osteoblasts, and osteoprogenitor cells. The artificial material may be formed to have porous surface. In addition, at least part of the bone matrix may be calcified. The osteoblasts and the osteoprogenitor cells may be differentiated cells obtained by culturing the mesenchymal stem cells derived from a living body.

The further aspect of the present invention includes a method for fabricating implant materials of the present invention. The method includes steps of culturing mesenchymal stem cells obtained from a living body to differentiate to at least one kind of cells selected from osteoblasts, and osteoprogenitor cells, and culturing the differentiated cells with a bioinert artificial material. As a result, the differentiated cells are adhered on the surface of the artificial material, and the surface of the artificial material is coated with bone matrix produced by the differentiated cells.

The method may further include a step of subculturing differentiated cells to increase the number of the cells.

Another method of the present invention includes steps of culturing mesenchymal stem cells obtained from a living body with a bioinert artificial material, adhering the mesenchymal stem cells to the surface of the artificial material, and differentiating the adhered mesenchymal stem cells to at least one kind of cells selected from osteoblasts and osteoprogenitor cells. As a result, the surface of the artificial material is coated with bone matrix produced by the differentiated cells.

DETAILED DESCRIPTION OF THE PREFERRED EMBODIMENTS

Figure 1:
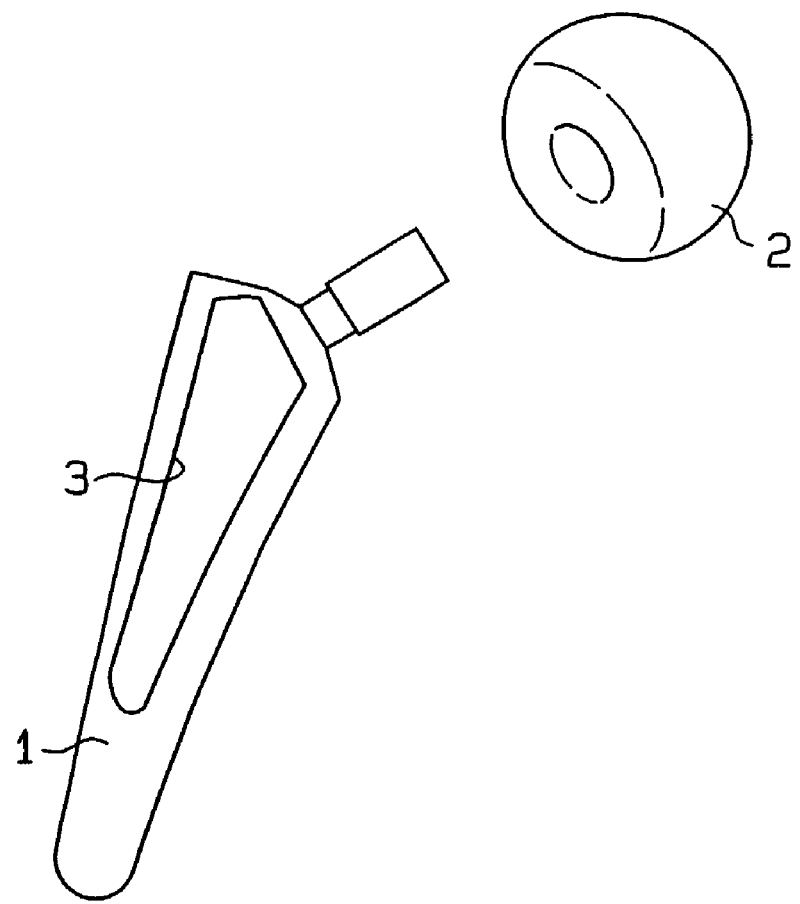
FIG. 1 illustrates a schematic view of an artificial joint, which is one of the artificial materials used as an implant material of the present invention, having a stem portion and an artificial head portion.

The present embodiments will be described below in detail.

Bone tissue is composed of bone matrix, and bone cells to which osteoblasts and osteoprogenitor cells differentiate. The bone cells are fixed on ossepus lacunae scattered in the bone matrix. The bone matrix is composed of relatively small amount of mucopolysaccharide proteins (proteoglycan), the main component of which is chondroitin sulfate, large amount of calcium phosphate, magnesium phosphate, calcium carbonate, and the like, and also contains various growth factors such as bone morphogenetic protein (BMP). In addition, the bone matrix normally contains considerable amount of collagen fibers, which give certain degree of resiliency to the bone. On the other hand, inorganic components such as apatite are formed by the action of osteoblasts (calcification of the bone matrix), which give hardness to the bone.

When the bone tissue is formed or remodeled, osteoblasts, osteoprogenitor cells, and osteoclasts, which exist at the circumference of the bone matrix, work, respectively. The osteoblasts and the osteoprogenitor cells are produced by the differentiation of the mesenchymal stem cells. The mesenchymal stem cells exist in bone marrow, and have very vigorous differentiating potency. Dexamethasone, which is one of steroid hormones, involves in vitro differentiation of the mesenchymal stem cells to osteoblasts, and osteoprogenitor cells.

The implant material of the present invention includes a bioinert artificial material implanted in a living body as a replacement of the bone tissue, which is obtained by the following steps. That is, at least one kind of cells selected from osteoblasts and osteoprogenitor cells are adhered to the surface of the artificial material, and the artificial material is coated with the bone matrix produced by the cells. The implant material may be used for a replacement of bone tissue when the bone tissue of a human, a pet, or a domestic animal are damaged, and may be implanted in a living body.

As used herein, "implanting" is defined as when an artificially fabricated material is surgically implanted in a living body.

The artificial material is used in various shapes as a replacement of the bone tissue. For example, the artificial material may include an artificial joint such as a hip joint, a knee joint, a finger joint, a shoulder joint, an elbow joint, and an ankle joint; a metallic artificial bone; an artificial bone made of synthetic resin; an artificial bone made of ceramics; volts (screw) for coupling bone tissues; prosthesis materials; dental implant materials; and bone connecting supplies.

The artificial materials may be composed of bioinert materials that are not degraded or decomposed in a living body, or the decomposition products of which do not adversely affect on a living body. The bioinert material is composed of materials other than bioactive materials, which can directly bond to bone tissue without using coating film (i.e., foreign film) when implanted in a living body as a replacement of the bone tissue, and also includes biotolerant materials and bioinert materials.

The biotolerant material includes materials that are separated from the tissues of a living body, with connective tissue thick film (i.e., foreign film) being formed between the bone tissues and the biotolerant material when it is implanted in the living body. For example, high-density polyethylene, stainless steel, and the like may be included. The bioinert material includes materials in which thin film (i.e., foreign film) is intervened between the bone tissues and the bioinert material when it is implanted in a living body, or may directly connect a part of the bone tissues under the favorable condition. For example, alumina ceramics, carbon ceramics, zirconia ceramics, titanium alloy, and the like may be included.

In addition, the artificial material is preferably composed of materials to which mesenchymal stem cells, osteoblasts, and osteoprogenitor cells are adhered to proliferate, and the surface of which is coated with bone matrix produced by these cells. At least one of the materials selected from titanium, titanium alloy, stainless steel, cobalt-chromium alloy, cobalt-chromium-molybdenum alloy, alumina ceramics, carbon ceramics, zirconia ceramics, silicon carbide ceramics, silicon nitride ceramics, glass ceramics, polyethylene, polystyrene, polytetrafluoroethylene, polyurethane, polyvinyl alcohol, polypropylene, polycarbonate, polymethyl methacrylate, methacrylate polymer, silicone resin and bioabsorbable polymer may be included as the above-mentioned material.

When the material is used as a replacement for bone tissue that requires greater strength, metallic materials such as titanium, titanium alloy, stainless steel, cobalt-chromium alloy, and cobalt-chromium-molybdenum alloy, or ceramic materials such as alumina ceramics, carbon ceramics, zirconia ceramics, silicon carbide ceramics, silicon nitride ceramics, and glass ceramics may be preferable.

When the material is used as a replacement for bone tissue that requires flexibility, elastically deformable synthetic resin materials such as polyethylene, polystyrene, polytetrafluoroethylene, polyurethane, polyvinyl alcohol, polypropylene, polycarbonate, polymethyl methacrylate, methacrylate polymer, silicone resin, and bioabsorbable polymer may be preferable.

The surface of the artificial material may be preferably porous. Because it is easy to enter mesenchymal stem cells, osteoblasts, and osteoprogenitor cells into pores of the material, and these cells are more stably fixed in the pores.

The surface of the bioinert artificial material may preferably be coated with bioactive substrate. As a result, the fixation of the osteoblasts and the osteoprogenitor cells and the production of bone matrix may further be promoted, and biocompatibility of the material may also be improved. The bioactive substrate includes calcium phosphates such as hydroxyapatite, tricalcium phosphate, calcium-deficient apatite, amorphous calcium phosphate, tetracalcium phosphate, octacalcium phosphate, fluorapatite, carbonate-apatite, calcium pyrophosphate, monetite, brushite; calcium carbonates; compounds that allow to adsorb calcium phosphates in a living body; compounds that allow to form an apatite layer on the surface of the material in a living body such as bioactive glass including glass-ceramics containing apatite, glass-ceramics containing calcium metaphosphate, and bioglass; and titanium, titanium alloy, and polymer materials, which allow to form an apatite layer by pseudo-body fluid dipping process.

The osteoblasts or the osteoprogenitor cells may preferably be obtained by culturing mesenchymal stem cells in a cultural solution containing differentiating inducing factor (dexamethasone), and differentiating them. Here, the mesenchymal stem cells may be proliferated by separating and culturing marrow cells obtained from a living body, which is scheduled to be implanted the implant material. This surely prevents adverse problems such as occurrence of rejection caused by autoimmunity after the implantation.

The surface of the artificial material may preferably be thickly coated with bone matrix to improve the biocompatibility after the implantation. More preferably, a part of the coated bone matrix may be calcified. In addition, the bone matrix may preferably contain a growth factor such as bone morphogenetic protein, which is secreted by at least one of cells selected from marrow cells, mesenchymal stem cells, osteoblasts, and osteoprogenitor cells. Since the growth factor promotes physiological adhesion, proliferation, and differentiation of mesenchymal stem cells of a living body in which the implant material was implanted, bone tissue repair speed and biocompatibility may be more improved.

The action of the implant materials will now be explained.

When the above implant material is fabricated, first an artificial material having a predetermined shape, which is used for a replacement of bone tissue, is prepared. Next, the surface of the artificial material is coated with bioactive substrate, such as hydroxyapatite using plasma spraying process, pseudo-body fluid dipping process, alternate dipping process, and the like. Subsequently, the coated artificial material is sterilized. Next, marrow cells are obtained using a syringe from a living body that is scheduled to be implanted. At this stage, it is preferable to increase the number of mesenchymal stem cells obtained from the marrow cells through well-known separating, culturing, or subculturing techniques.

Subsequently, the marrow cells or the mesenchymal stem cells are adhered to the artificial material, and the resultant material is cultured in a solution containing dexamethasone, β-sodium glycerophosphate, and ascorbic acid, and the cells adhered to the artificial material are differentiated to osteoblasts and osteoprogenitor cells. Then, the surface of the artificial material is coated with bone matrix produced by these cells. Alternatively, the marrow cells or the mesenchymal stem cells may be cultured in the culture solution in advance to differentiate to osteoblasts and osteoprogenitor cells. The resultant osteoblasts and osteoprogenitor cells may be cultured with a sterilized artificial material. As a result, these cells may adhere to the surface of the artificial material, and the surface of the artificial material may be coated with bone matrix produced by these cells.

When the marrow cells or the mesenchymal stem cells are cultured with the artificial material to differentiate, a cell-suspended solution containing the marrow cells or the mesenchymal stem cells is prepared, and then an artificial material is soaked in the cell-suspended solution. As a result, the cells are adhered to the surface of the artificial material soaked in the solution. Subsequently, the artificial material is cultured in the solution. The marrow cells or the mesenchymal stem cells adhered to the artificial material proliferate at the surface of the artificial material, and then differentiate to osteoblasts and osteoprogenitor cells. The differentiated osteoblasts and osteoprogenitor cells extracellularly produce bone matrix. The surface of the artificial material is directly coated with the bone matrix without being intervened with a foreign film.

Alternatively, when the marrow cells or the mesenchymal stem cells are differentiated to the osteoblasts and the osteoprogenitor cells in advance, and then the differentiated cells are cultured with the artificial material, the marrow cells or the mesenchymal stem cells are initially cultured in a culture dish, which fills with the culture solution. These cells quickly proliferate while adhering on the bottom surface of the culture dish since they have high proliferation potency. Subsequently, when these cells are cultured in the culture solution, they are differentiated to a large number of osteoprogenitor cells and osteoblasts. If necessary, subculture is performed to additionally increase the number of cells. After the number of the osteoblasts and the osteoprogenitor cells sufficiently increases, these cells are detached from the bottom surface of the dish using trypsin solution or the like, and then suspended in the culture solution to prepare a cell-suspended solution. Subsequently, the artificial material is soaked in the cell-suspended solution, and then incubated in an incubator. Here, some osteoblasts and osteoprogenitor cells adhere to the surface of the artificial material soaked in culture solution, and then grow on its surface. Then, the cells produce bone matrix. The resultant bone matrix is directly coated on the surface of the artificial material without a foreign film being intervened.

When the above implant material is implanted in a living body as a replacement of bone tissue, the surface of the implant material is coated with cells of a living body itself and bone matrix derived from the living body to be implanted. Therefore, the implanted material has considerably high biocompatibility for adjacent bone tissues, other tissues, and cells. In addition, since the bone matrix is coated on an entire surface of the implant material, the living body does not recognize implant material as a foreign body, and occurrence of inflammatory reaction and formation of coated film (i.e., foreign film) can be avoided.

In addition, the osteoblasts and the osteoprogenitor cells that are adhered to the surface of the implant material in advance have already high bone repair activity at the time when implanted. Therefore, new bone formation is started while the circumference of the implanted material is coated with the bone matrix immediately after the implantation. With the passage of the time, the clearance between the implant material and bone tissues surrounding the implant material is minutely filled with the cells to repair the bone, and then the implant material is more surely fixed.

Also, the bone matrix produced on the surface of the implant material promotes physiological adhesion and growth of the pluripotent mesenchymal stem cells, osteoblasts, and osteoprogenitor cells of the living body. Therefore, these cells are physiologically adhered to the implant material after implantation. These cells start the bone repair process and new bone matrix is deposited to the implant material. This achieve reliable fixation of the implant material in the bone tissue.

After additional period of time passes, repaired bone tissues that surround the implant material would continually maintain the condition that is always and properly renewed by the physiological metabolism of the living body through the work of the osteoclasts, the osteoprogenitor cells, and the osteoblasts. If this condition is maintained, either looseness or disengagement of the implant material rarely occurs for a long time use.

The above embodiments of the present invention have the following effects.

The implant material of the present embodiment is obtained by the steps of adhering at least one kind of cells selected from osteoblasts and osteoprogenitor cells to the surface of a bioinert artificial material, which is implanted in a living body as a replacement of bone tissue, and coating with bone matrix produced by the adhered cells. Since the bioinert material is used as the artificial material, it is possible to easily and surely give desired mechanical properties (mechanical strength, abrasion resistance, and the like) for an implant material. That is, the implant material may be selected based on wide variety of usages, such as a replacement for bone tissues having high mechanical strength, bone tissues having elastic deformability, and the like.

Since the cells having greater bone repair ability are adhered to the surface of the implant material, they fill the clearance between the implant material and bone tissues surrounding the implant material from immediately after the implantation, and the speed of bone tissue repair is increased. There are many cases in which bone tissue repair speed in vivo is slow in an aged organism. Even in such a case, early treatment and fixation of the implant material may surely be achieved by adhering cells with artificially enhanced bone repair activity. Therefore, the time required for complete recovery may be reduced, the period for incurring the bodily and mental suffering may also be reduced, and the cost for the treatment may be reduced.

In addition, since the bone matrix produced by the osteoblasts and the osteoprogenitor cells are coated on the surface of the implant material, the biocompatibility may be improved without a film (a foreign film) being formed between surface of the implant material and bone tissues surrounding the implant material. Therefore, it is possible to maintain high biocompatibility of the implant material in vivo for a long period of time from immediately after the implantation. Also, physiological adhesion and growth of pluripotent mesenchymal stem cells, osteoblasts, and osteoprogenitor cells in vivo are facilitated.

As mentioned above, according to the present invention, early treatment and early fixation of the implant material to the bone tissues are easily and surely achieved. In addition, the implanted material may be used for a long period of time without any troubles.

In the conventional artificial joint, PMMA bone cement or an artificial material, which is a bioinert material, directly contacts the bone tissues. Therefore, there was a remarkably high possibility that film was formed on the surface of the artificial joint and the failure, such as looseness or disengagement of the artificial joint, occurs. However, the implant material of the present embodiments drastically raises the biocompatibility due to the bone matrix coated on the surface of the implant material. As the result, looseness and disengagement of the artificial joint rarely happen, and the implanted material may use for a long period of time without any troubles.

In addition, since the PMMA bone cement generates very high heat of polymerization, the bone tissue receives serious damages when contacting the bone cement. As the result, the biocompatibility between bone cement and bone tissues surrounding the artificial joint drastically lowered, and the burden for a living body remarkably increased. In contrast, the implant material of the present embodiments has very much increased bone repair activity. Therefore, without using bone cement, the early fixation of the implant material can be achieved using the natural healing power of a living body. Therefore, the above problems of heat of polymerization may be easily and surely solved. In addition, the problems of harmful residual monomer, which occur during the polymerization of the PMMA bone cement, may be surely solved.

In the conventional implant material such as an artificial joint, it has been studied that the bone repair activity was raised by administering biological factors such as cytokine, which is an expensive drug in the treatment. On the other hand, since osteoblasts and osteoprogenitor cells having raised bone repair activity are adhered to the implant material of the present embodiments, and since it is not necessary to administrate the above biological factor, the present embodiments are economical. In addition, the burden for post-operative care may be alleviated.

Conventionally, bone autograft substitute has been performed, in which bone tissue such as an iliac bone is obtained from a living body that is scheduled to be implanted and then is implanted into the living body as a replacement for damaged bone tissue. However, an extra operation is necessary for obtaining bone tissue other than damaged tissue in this bone autograft substitute. On the other hand, according to the present invention, it is only necessary to perform an operation with small burden in which marrow cells are obtained using a syringe. Therefore, the above extra operation is not necessary, and the physical and mental suffering of the living body to be implanted may also be reduced.

Bone matrix of the implant material may further include biological factor, such as growth factor secreted from at least one kind of cells selected from marrow cells, mesenchymal stem cells, osteoblasts, and osteoprogenitor cells. As a result, physiological adhesion and proliferation of mesenchymal stem cells of a living body in which the implant material was implanted and differentiation to osteoblasts and osteoprogenitor cells are promoted. In addition, even if cells adhered to the surface of the implant material are accidentally dead, bone matrix and the biological factor contained in the bone matrix promotes the physiological adhesion of the mesenchymal stem cells existing in the implanted living body. Therefore, bone tissue repair speed and biocompatibility are enhanced.

The artificial material is composed of at least one of materials selected from titanium, titanium alloy, stainless steel, cobalt-chromium alloy, cobalt-chromium-molybdenum alloy, alumina ceramics, carbon ceramics, zirconia ceramics, silicon carbide ceramics, silicon nitride ceramics, glass ceramics, polyethylene, polystyrene, polytetrafluoroethylene, polyurethane, polyvinyl alcohol, polypropylene, polycarbonate, polymethyl methacrylate, methacrylate polymer, silicone resin and bioabsorbable polymer. As a result, degradation or decomposition of the implant material in vivo, or the adverse effects of the decomposed products from the implant material on a living body are avoided, and sure role as a replacement for damaged bone tissue is performed.

In addition, since most suitable material for treatment is properly selected from a wide variety of the materials, an implant material having desired mechanical property is obtained. More particularly, since the artificial material composed of metallic material and ceramic material has high mechanical strength, it is suitable for a replacement of bone tissue that requires high mechanical strength. Artificial material made of ceramics is made to easily form one having porous surface. Therefore, a weight saving of an implant material may be achieved. Artificial material made of elastically deformable synthetic resin is suitable for a replacement of the bone tissue that requires flexibility.

Bioinert artificial material may promote implantation, growth, and bone repair of mesenchymal stem cells, osteoblasts, and osteoprogenitor cells, when the bioactive substrate is coated on the surface of the artificial material.

It is possible to surely prevent the rejection by the autoimmunity of an implanted living body by using, as cells to be adhered to the implant material, osteoblasts and osteoprogenitor cells obtained by differentiating cultured mesenchymal stem cells derived from a living body scheduled to be implanted.

Even if the mesenchymal stem cells are those obtained from an aged living body, it is possible to culture the cells in vitro to proliferate them. As a result, they have almost the same proliferating and differentiating potency, as well as bone repair activity, as those derived from a young living body, and excellent therapeutic effects are achieved in the aged living body.

By designing the surface of an artificial material to be porous, it is possible that mesenchymal stem cells, osteoblasts, and osteoprogenitor cells easily enter the pores of the artificial material, and these cells are fixed in a stable condition. Since the superficial area increases in the porous artificial material, it is possible to fix more cells to the implant material. It is also possible to avoid looseness and disengagement of the implant material, since the larger area and the more complicated shape of the porous implant material contact bone tissues surrounding the implant material after the bone repairing.

Calcification of the bone matrix achieves very firm bonding between the implant material and the bone tissues surrounding the implant material. Accordingly, biocompatibility of the implant material is more enhanced, and the period until complete recovery is remarkably reduced.

The method for fabricating the implant material according to the present embodiments includes the steps of culturing mesenchymal stem cells obtained from a living body to differentiate to at least one kind of cells selected from osteoblasts and osteoprogenitor cells, and culturing the differentiated cells with a bioinert artificial material. As a result, the differentiated cells are adhered to the surface of the artificial material, and the surface of the artificial material is coated with bone matrix produced by the differentiated cells. The above method easily achieves the production of the implant material having the desired mechanical property and improved bone tissue repair speed and biocompatibility.

EXAMPLES

The present invention will now be described with reference to the following examples in which the above-mentioned embodiments are embodied, and comparative examples.

Subcutaneous Implantation Experiment

Example 1

Marrow cells were obtained from a bone shaft of femurs of 7 week-old male Fischer rats, and α-MEM (minimum essential medium) containing 15% of fetal bovine serum (FBS) was added to the cells, and then obtained culture was primarily cultivated in an incubator (37° C., an atmosphere of 5% $CO_2$) for 7–12 days.

After the primary culture, the cultured marrow cells were treated with 0.01% of trypsin solution, and $1 \times 10^6$ to $1 \times 10^7$ cells/ml of cell suspension was prepared. Disk artificial materials having a diameter of 34 mm and a thickness of 2 mm (made of titanium alloy, stainless steel, alumina ceramics and high-density polyethylene) were soaked in the suspension, and were incubated in an incubator for two hours (37° C., an atmosphere of 5% $CO_2$). Porous artificial materials having a rectangular parallelepiped shape (3×3×5 mm) (made of titanium alloy, stainless steel, alumina ceramics and high-density polyethylene) were soaked in the suspension, and were incubated in an incubator for about 2 hours, as described in the above procedure.

Subsequently, these materials were transferred to a 35 mm culture dish, to which 2 ml of medium containing antibiotics, $10^{-8}$ M of dexamethasone, 10 mM of β-sodium glycerophosphate, and 50 µg/ml of ascorbic acid was added, and were incubated for about one week (37° C., an atmosphere of 5% $CO_2$). If necessary, the medium was changed.

It was confirmed by alkaline phosphatase activity and alizarin red stain that the osteoprogenitor cells and the osteoblasts differentiated from the mesenchymal stem cells derived from bone marrow were adhered to the surface of the implant material, and the surface thereof was coated with bone matrix produced by these cells. In addition, the experiment in which the porous implant material was implanted in the back hypodermic of syngeneic rats was performed. About one to two weeks later, new bone formation was confirmed on the surface of the implant material.

Comparative Example 1

Four kinds of artificial materials (titanium alloy, stainless steel, alumina ceramics, and high-density polyethylene) were directly implanted in the back hypodermic of the rats. As a result, the intervention of fibrous tissue (a foreign film) surrounding the artificial materials was confirmed in the early stage after the implantation, and new bone formation was never confirmed.

Artificial Joint Using Test

Example 2

Marrow cells were obtained from an adult dog, and were primarily cultured for 7–12 days, as is like Example 1. After cultivation, a cell-suspended solution was prepared. The stem portion of the artificial hip joint composed of titanium alloy was soaked in the cell-suspended solution, and was incubated for two hours (37° C., an atmosphere of 5% $CO_2$) Subsequently, the stem portion was transferred to a culture container containing culture medium identical to the medium used in example 1, and was cultured in an incubator (37° C., an atmosphere of 5% $CO_2$) for about 1 week. If necessary, the medium was changed.

It was confirmed that the osteoprogenitor cells and the osteoblasts differentiated from the mesenchymal stem cells derived from bone marrow were adhered to the surface of the implant material, and the surface thereof was coated with bone matrix produced by these cells. In addition, when the stem portion of the artificial hip joint was implanted into a cavity of the femur of the adult dog, fixation between the stem portion and the femur was confirmed. In the artificial hip joint, new bone formation was confirmed on the surface of the stem portion in early stage after the implantation, and the fixation of the stem was also quickly finished.

Comparative Example 2

An artificial hip joint without being soaked in the cell-suspended solution was implanted as is like in example 2. As a result, partial fixation between the stem portion and the femur was observed, and was resulted in the looseness of the stem portion.

Example 3

2 ml of marrow cells were obtained from a humerus of a beagle dog having 12 kg of body weight. The obtained marrow cells were transferred to a tube containing 2 ml of FBS with heparin, and were centrifuged (900 rpm, 10 minutes, 24° C.) After fat cells and supernatant were removed from the centrifuged tube, cells were transferred to a T-75 flask, and were primary-cultured in a medium containing 15% of FBS and antibiotics for ten days. The culture medium was exchanged 3 times per week.

In this embodiment, an implant material having a stem 1 made of titanium (hereafter referred as "Ti") and an artificial head 2 made of high purity alumina were used as shown in FIG. 1. Both surfaces of the stem 1 include associated recesses 3 (depth; 0.5 mm, area; 1.3 $cm^2$). The implant material was treated with thermal spraying processing of pure Ti. Average surface roughness of the thermal spraying plane was 32 $\mu$m. After the primary culture, 0.25% of trypsin was used for detachment processing, and a cell-suspended solution was prepared.

A stem for a dog was put in the culture dish having a 94 mm diameter, and $1\times10^5$ cells of the cell-suspended solution was put on a surface to be treated with the pure Ti thermal spraying processing (area; 1.3 $cm^2$) of upper stem side, and incubated at 37° C. for 30 minutes to adhere the cells to the surface to be treated with the Ti thermal spraying processing. Subsequently, 48 ml of medium containing 10 mM of $\beta$-glycerophosphate, 82 $\mu$g/ml of vitamin C phosphate, and $10^{-8}$ M of dexamethasone was added to carry out the subculture for 11 days.

When subcultured stem was stained using a stain for an alkaline phosphatase, a surface treated with Ti thermal spraying processing in which the cells were seeded was stained in red. On the other hand, a surface treated with Ti thermal spraying processing in which the cells were not seeded, i.e., the rear side of the stem, was not stained. This means that cells differentiated to the osteoblasts existed on an entire surface in which the cells were seeded.

A line from greater trochanter to lesser trochanter at femur head side of a right femur of a beagle dog was made to incision, and the femur head was extracted. Rasping was performed using medullary cavity expansion and trial. Surfaces of the stem, in which the above prepared cells were mounted on one side, was washed with PBS (−) and physiological saline solution. Subsequently, the stem was inserted into a medullary cavity of the femur, and an artificial bone head was attached to the stem.

The dog was sacrificed three weeks after the operation, and the implanted stem portion was extracted. The surface of the stem, which is treated with the Ti thermal spraying processing, was histologically observed. The Ti spraying surface in which the cells were mounted was observed that new bone was formed in the cavity of the Ti spraying surface, the entire surface in which the cells were mounted was covered with the new bone. On the contrary, the Ti spraying surface in which the cells were not mounted was observed that the stem was partially contacted with the bone.

The present embodiments may be embodied with following modifications.

The artificial material may be composed of the combination of metallic material or ceramic material with synthetic resin. For example, in the artificial joint consisting of a stem portion, a head portion, and an acetabular portion, the stem portion and the head portion may be made of the metallic material or the ceramic material, while the acetabular portion may be made of the synthetic resin material. The above composition achieves an implant material in which each part has its optimal mechanical properties. Therefore, it is possible to reduce discomfort for a living body.

The surface of an implant material made of bioinert material may not be coated with bioactive substrate. Even when the above implant material is used, the mesenchymal stem cells, osteoblasts, and osteoprogenitor cells may be adhered to the surface of the artificial material, and the surface of the artificial material may be coated with bone matrix produced by the osteoblasts and the osteoprogenitor cells.

The surface of the artificial material may not be formed porous, but be flat. The artificial material with a flat surface may easily be molded.

The implant material may be constituted of an artificial material that includes bioinert material in which mesenchymal stem cells, osteoblasts, and osteoprogenitor cells could not be adhered and proliferated, and is coated with a bioactive substrate on the surface of the artificial material. The above implant material may allow to adhere at least one kind of cells selected from the osteoblasts and the osteoprogenitor cells to the surface of the implant material, and may be coated with the bone matrix.

As an osteoblast or a osteoprogenitor cell to be adhered to the surface of the implant material, cells derived from homogeneous biological organisms having identical major histocompatibility complex (MHC), or human lymphocyte antigen (HLA) may be used. Alternatively, cells that do not have identical MHC or HLA may be used, while the immunosuppressant may be administered. When the above cells are used for an implant material, it is possible to surely suppress the rejection by autoimmunity. When marrow cells of a living body scheduled to be implanted are suspicious of cancerous, it is afraid that innidiation and metastasis of the cancer is promoted by implanting an implant material in which cells derived from the cancerous marrow cells are adhered to such a living body. However, the above possibility may be avoided by using marrow cells obtained from a healthy, non-cancerous organism. In addition, when a cord blood, more specifically, the mesenchymal stem cells included in the cord blood may be used, it is very advantageous.

A part of the mallow cells or the mesenchymal stem cells may be cultured in the cultural solution with the artificial material, and the remainder may be cultured on the culture dish. After the number of the cells on the culture dish increases, the cells may be adhered to the surface of the artificial material, and then cultured. In addition, a part of cells, the number of which is increased by the subculture, may be adhered to the surface of the artificial material and be cultured, and the remaining cells may further be subcultured. After the number of the subcultured cells increases, the subcultured cells may be adhered to the surface of the artificial material, and be cultured. The above construction may efficiently increase the number of osteoblasts and osteoprogenitor cells in a short period of time. This greatly shortens the period for fabricating the implant material. In addition, more cells may be adhered to the surface of the implant material.

The implant material may be fabricated using an artificial material molded on the shape that conforms to a bone defective part or a bone vacant part, and the resultant implant material may be implanted on the bone defective part or the bone vacant part. The above implant material may give the desired mechanical properties, and improve the bone tissue repair speed and the biocompatibility.

As a differentiating inducing factor for differentiating mesenchymal stem cells to osteoblasts and osteoprogenitor cells, bone morphogenetic protein, fibroblast growth factor, glucocorticoid or prostaglandin may be used.

At least one growth factor selected from dexamethasone, bone morphogenetic protein, fibroblast growth factor, glucocorticoid, and prostaglandin may be attached to, adhered to, or soaked in the surface of the implant material. The above implant material may further be enhanced its bone repair activity.

What is claimed is:

1. A bone tissue implant comprising a bioinert artificial material and osteoblast cells or non-embryonic osteoprogenitor cells, adhered directly on the material, whereby a bone matrix produced by the cells in vitro coats the material.

2. The implant according to claim 1, wherein the material comprises titanium, titanium alloy, stainless steel, cobalt-chromium alloy, cobalt-chromium-molybdenum alloy, alumina ceramics, carbon ceramics, zirconia ceramics, silicon carbide ceramics, silicon nitride ceramics, glass ceramics, polyethylene, polystyrene, polytetrafluoroethylene, polyurethane, polyvinyl alcohol, polypropylene, polycarbonate, polymethyl methacrylate, methacrylate polymer, silicone resin, or a bioabsorbable polymer.

3. The implant according to claim 1, wherein the material comprises titanium, titanium alloy, stainless steel, cobalt-chromium alloy, or cobalt-chromium-molybdenum alloy.

4. The implant according to claim 1, wherein the material comprises alumina ceramics, carbon ceramics, zirconia ceramics, silicon carbide ceramics, silicon nitride ceramics, or glass ceramics.

5. The implant according to claim 1, wherein the material comprises polyethylene, polystyrene, polytetrafluoroethylene, polyurethane, polyvinyl alcohol, polypropylene, polycarbonate, polymethyl methacrylate, methacrylate polymer, silicone resin, or a bioabsorbable polymer.

6. The implant according to claim 1, wherein the bone matrix comprises a growth factor secreted from marrow cells, mesenchymal stem cells, osteoblast cells, or osteoprogenitor cells.

7. The implant according to claim 1, wherein the material comprises a porous surface.

8. The implant according to claim 1, wherein at least part of the bone matrix is calcified.

9. The implant according to claim 1, wherein the cells are obtained by culturing and then differentiating the mesenchymal stem cells derived from a living body.

* * * * *